(12) United States Patent
Baru et al.

(10) Patent No.: US 10,842,996 B2
(45) Date of Patent: Nov. 24, 2020

(54) NEURAL STIMULATION AND RECORDING, PARTICULARLY FOR NEUROMODULATION CLOSED-LOOP CONTROL

(71) Applicant: BIOTRONIK SE & Co. KG, Berlin (DE)

(72) Inventors: Marcelo Baru, Tualatin, OR (US); Andrew B. Kibler, Lake Oswego, OR (US)

(73) Assignee: BIOTRONIK SE & Co. KG, Berlin (DE)

(*) Notice: Subject to any disclaimer, the term of this patent is extended or adjusted under 35 U.S.C. 154(b) by 189 days.

(21) Appl. No.: 16/032,701

(22) Filed: Jul. 11, 2018

(65) Prior Publication Data

US 2019/0030339 A1  Jan. 31, 2019

Related U.S. Application Data

(60) Provisional application No. 62/537,003, filed on Jul. 26, 2017.

(51) Int. Cl.
*A61N 1/36* (2006.01)
*A61B 5/04* (2006.01)
(Continued)

(52) U.S. Cl.
CPC ...... *A61N 1/36132* (2013.01); *A61B 5/04001* (2013.01); *A61B 5/4035* (2013.01); *A61B 5/4836* (2013.01); *A61B 5/686* (2013.01); *A61B 5/6877* (2013.01); *A61B 5/7217* (2013.01); *A61N 1/0551* (2013.01); *A61N 1/3605* (2013.01); *A61N 1/36114* (2013.01); *A61N 1/36139* (2013.01); *A61N 1/36164* (2013.01); *A61B 5/4041* (2013.01); (Continued)

(58) Field of Classification Search
None
See application file for complete search history.

(56) References Cited

U.S. PATENT DOCUMENTS 7,203,548 B2 * 4/2007 Whitehurst .......... A61N 1/0556
607/118
8,454,529 B2   6/2013 Daly et al.
(Continued)

OTHER PUBLICATIONS

Blum et al., "Models of Stimulation Artifacts Applied to Integrated Circuit Design", Proceedings of the 26th Annual International Conference of the IEEE EMBS, pp. 4075-4078, Sep. 2004.
(Continued)

*Primary Examiner* — Brian T Gedeon
(74) *Attorney, Agent, or Firm* — Buchanan Ingersoll & Rooney PC (57) ABSTRACT

A device for neurostimulation including an electrode structure for delivering stimulation pulses to a nerve as well as for processing and extracting evoked compound action potentials, wherein the electrode structure comprises at least a first anode, at least a second anode opposing the first anode and a plurality of cathodes arranged between said anodes, wherein said cathodes are asymmetrically arranged with respect to said at least first and second anode to permit evoked compound action potential sensing via the anode electrodes simultaneously with stimulation.

16 Claims, 9 Drawing Sheets

(51) Int. Cl.
  *A61N 1/05* (2006.01)
  *A61B 5/00* (2006.01)
  *A61N 1/37* (2006.01)

(52) U.S. Cl.
  CPC .......... *A61B 5/4094* (2013.01); *A61B 5/6869* (2013.01); *A61N 1/0553* (2013.01); *A61N 1/0556* (2013.01); *A61N 1/36036* (2017.08); *A61N 1/3716* (2013.01)

(56) References Cited

U.S. PATENT DOCUMENTS

| | | | | |
|---|---|---|---|---|
| 8,504,161 | B1 * | 8/2013 | Kornet | A61N 1/36053 |
| | | | | 607/118 |
| 9,895,542 | B2 * | 2/2018 | Baru | A61N 1/0556 |
| 2015/0290461 | A1 * | 10/2015 | Min | A61N 1/36135 |
| | | | | 607/59 |

OTHER PUBLICATIONS

Nag et al., "Sensing of Stimulus Artifact Suppressed Signals from Electrode Interfaces", IEEE Sensors Journal, vol. 15, No. 7, pp. 3734-3742, Jul. 2015.

Hughes, Michelle L., "Fundamentals of Clinical ECAP Measures in Cochlear Implants: Part 1: Use of the ECAP in Speech Processor Programming (2nd Ed.)", AudiologyOnline, 14 pages, Nov. 2010.

* cited by examiner

NEURAL STIMULATION AND RECORDING, PARTICULARLY FOR NEUROMODULATION CLOSED-LOOP CONTROL

CROSS-REFERENCE TO RELATED APPLICATIONS

This patent application claims the benefit of U.S. Provisional Patent Application No. 62/537,003, filed on Jul. 26, 2017, which is hereby incorporated by reference in its entirety.

BACKGROUND

Unlike cardiac myocyte depolarizations, neuronal depolarizations typically last one millisecond or less, and when sensed with far-field electrodes, develop amplitudes in the tens of microvolts.

In order to confirm neural activation as a result of stimulation, it is desired that these signals be observed immediately following stimulation or even while stimulation is being delivered. However, stimulation is typically associated with and accompanied by volt-level stimulation artifacts which may have frequency components similar to that of the evoked neural potentials.

The stimulation artifact (SA) is a direct consequence of the accumulated charge in the electrode-tissue interface during stimulation. A common approach is to employ charge-balanced biphasic stimulation in the hope that the symmetric nature of the stimulation will eliminate the SA. Unfortunately, Faradaic reactions are typically required to elicit a physiological response via electrical stimulation.

This may imply that not all of the charge injected in a stimulation pulse is accumulated in the electrode-tissue double layer, due to the fact that perfectly reversible processes are unlikely. Hence, charge-balanced operation forces the electrode in these cases to a more positive potential than its original open circuit potential (OCP) thus not eliminating the SA.

Dedicated circuitry at each electrode has been proposed to provide discharge paths post stimulation to return the electrode potential close to the OCP prior to stimulation (Blum et al., "Models of Stimulation Artifacts Applied to Integrated Circuit Design", Proceedings of the 26th Annual International Conference of the IEEE EMBS, 4075-78, September 2004).

Further, U.S. Pat. No. 8,454,529 discloses utilizing a compensatory stimulus (third phase) instead following biphasic stimulation in order to counteract the SA. U.S. Pat. No. 8,454,529 also discloses short-circuiting the stimulating electrodes for a very short period of time (approximately 1 µs) preferably immediately following the delivery of the compensatory stimulus.

An improved SA suppression scheme using two-electrode simultaneous stimulation, a reference electrode, and differential readout has also been proposed (Nag et al., "Sensing of Stimulus Artifact Suppressed Signals from Electrode Interfaces", IEEE Sensors Journal, vol. 15, no. 7, pp. 3734-42, July 2015).

Additional methods known to permit evoked compound action potential (ECAP) recording include placing sensing electrodes distant from the site of stimulation but adjacent to the stimulated nerve so that the SA has settled to low amplitude by the time the ECAP propagates past the recording electrodes. This method is commonly used in pre-clinical studies where large portions of the nerves of interest may be accessed.

Direct current (DC) blocking capacitors are an important safety feature in the design of implantable pulse generators (IPGs). They are primarily placed to limit the charge per phase, reduce DC leakage and prevent DC from circulating through tissue under a fault condition, among other functions. Although various approaches have been proposed in the prior art for their elimination, given their typical sizes, reduced safety remains a concern and the reason why they continue to be employed in the design of IPGs for chronic human implants. Placing dedicated circuitry with a DC path to an electrode as described in Blum et al. (see above) for the purpose of returning the electrode voltage to the open circuit potential (OCP) defeats in a sense the purpose of the DC blocking capacitors, requiring single-fault protected circuitry with tight leakage requirements (100 nA maximum) and adding non-negligible extra time for compensation. Hence, it is not a preferred solution for chronic implantation in a clinical product. Forcing the electrode back to a known potential post biphasic stimulation is actually a consequence of poor charge balancing as traditional charge-balanced stimulation typically over-compensates the electrode potential return past zero volts.

Finding a compensatory electrical stimulus as proposed in U.S. Pat. No. 8,454,529 which may involve a monophasic electrical stimulus (or a biphasic stimulation with a third compensatory phase) assumes that the large stimulation artifact (SA) voltage does not saturate the evoked compound action potential (ECAP) recording front-end which may not be the case. Using a third compensatory phase is similar to using dedicated circuitry to return the voltage to a certain level post biphasic stimulus. The need to use such strategies is a consequence of charge over-compensation during biphasic stimulation.

The improved SA suppression scheme using two-electrode simultaneous stimulation, a reference electrode, and differential readout proposed in Nag et al. (see above), besides using charge-balanced stimulation which typically over-compensates the electrode potential return as mentioned above, requires an extra "active" stimulating electrode, and this extra electrode is to be matched (in terms of impedance) to the original stimulating electrode to reject the SA. Impedance mismatch, caused by electrode-electrolyte interface differences, is disclosed to be compensated via in-series circuitry (e.g., resistor and capacitor). This would require adaptive compensation as the electrode-electrolyte interface changes with time and hence it is not a preferred solution. Further, Nag et al. utilize DC-coupled differential recording which is not desired for the reasons mentioned above. Preferably, an improved SA rejection scheme does not require an additional electrode for operation.

Furthermore, placing ECAP recording electrodes far from the stimulation site is proposed in the prior art which requires greater surgical access to the nerve, often requiring much larger incision sites, additional surgical manipulation, and greater risk of infection and nerve damage in the case of peripheral nerves. In the case of a peripheral nerve cuff (e.g., vagus nerve stimulation, VNS), greatly expanded surgical access is required, such that most commonly, recording electrodes are not implanted and the therapy suffers from a lack of closed-loop feedback. For the application of spinal cord stimulation (SCS), this typically requires the recording electrodes to be placed at the proximal or distal electrode areas of a spinal cord stimulation lead or in a separate lead. For the case of deep brain stimulation (DBS), activation responses (second and third-order) from neurons other than the primary neurons of interest must be found and decoded; currently no device on the market supports this.

Evoked compound action potentials (ECAPs) show promise for the implementation of closed-loop neuromodulation applications. However, for robust therapy delivery, there is a need for systems and methods that can provided consistent ECAP recording using electrodes physically close to the site of stimulation, or electrodes that even participate in stimulation, and allow recording at high fidelity temporally very close to the time of stimulation.

The present invention is directed at overcoming one or more of the above-mentioned problems.

SUMMARY

A problem to be solved by the present invention is therefore to provide a device for neurostimulation that is capable of allowing microvolt-level recordings during or immediately following volt-level stimulation without prolonging the charge-balance phase and thereby maintaining stimulation safety.

It is a further objective of the present invention to provide a sensing configuration, and a compensation method that permits recording during stimulation without blanking and without "additional" electrodes.

Yet another objective of the present invention is to propose a method to record any remnant stimulation artifact (SA) that may be present, including the front-end sensing amplifier transient response caused by stimulation (residual SA), for subsequent subtraction from a signal that includes the ECAP of interest.

A problem underlying the present invention is solved by a device having the features of claim 1.

According thereto, a device for neurostimulation comprising an electrode structure for delivering stimulation pulses to a nerve as well as for receiving evoked compound action potentials is disclosed, wherein the electrode structure comprises a first anode, a second anode opposing the first anode and at least one cathode arranged between said anodes, wherein said cathode(s) are asymmetrically arranged with respect to said first and/or second anode.

Further, the present invention discloses devices and methods for stimulation artifact (SA) elimination using particularly a multi-stage mixed-domain approach. For this, a balance phase of a stimulation pulse/phase may be automatically determined to return the electrode potential post stimulation close to the open circuit potential (OCP) to minimize the SA.

Further, the stimulation utilizes an asymmetric guarded-cathode configuration where current sources are forced via the anodes. The anodes are connected to the inputs of an AC-coupled sensing front-end. Mismatches between the different electrode-tissue impedances, and sensing components, may be compensated via adjustment of the current sources flowing through the anodes to have similar voltage profiles at the inputs of the sensing front-end. These signals are seen as common mode by the latter, which can then reject them by its high common mode rejection ratio (CMRR). This results in a "recordable" SA (i.e., amplifier is not saturated and of amplitude comparable to the ECAP to be recorded). Hence, particularly, no "extra" circuitry is placed in series with the desired stimulation configuration.

Further, it is well-known that neurons have a threshold of activation under which they cannot fire an action potential as a result of stimulation. Stimulation with amplitude below this level is referred to as sub-threshold stimulation. Above the amplitude required to activate neurons, stimulation is referred to as supra-threshold.

In an embodiment of the present invention, the residual SA is first recorded and digitized utilizing a sub-threshold pulse followed by a supra-threshold and the two subtracted to obtain the desired evoked compound action potential (ECAP). The time between the two pulses is such that the impedances can be considered invariant.

Furthermore, according to yet another aspect/embodiment of the present invention, a forward-masking subtraction method as utilized in cochlear implants (Hughes M., "Fundamentals of Clinical ECAP Measures in Cochlear Implants: Part 1: Use of the ECAP in Speech Processor Programming (2nd Ed.)", AudiologyOnline, November 2010). (http://www.audiologyonline.com/articles/fundamentals-clinical-ecap-measures-in-846)) can be utilized to isolate the residual SA. Here, particularly, this method utilizes two supra-threshold pulses, i.e., a probe pulse and a masker pulse. A probe pulse is delivered first and the SA plus ECAP recorded and digitized. A masker pulse followed by a probe pulse is delivered next. The time between the masker and probe pulses is such that the latter is delivered during the refractory period of the fibers recruited by the former. In this way, the masker pulse only generates a residual SA which is recorded and digitized. The digitized signal that contains the residual SA plus ECAP is then subtracted from this latter digitized signal that only contains the residual SA to obtain the desired ECAP.

According to yet another aspect/embodiment of the present invention, an analog SA simulation circuit is iteratively tuned via feedback through an analog-to-digital converter (ADC) under the control of the implantable pulse generator's (IPG) control unit. The tuning adjusts the analog SA simulator so that it generates waveforms which match the sub-threshold (and later, supra-threshold) SA. The output of this analog SA simulation circuit is then subtracted from the received analog signal, resulting in a signal comprised mainly of ECAPs (if stimulation is supra-threshold).

In the following, further embodiments, as well as particular features of the above-described aspects/embodiments of the present invention, are described.

According to an embodiment of the device according to the present invention, the two anodes are coaxially arranged with respect to an axis, and wherein the cathodes are arranged spaced apart from said axis (A).

Further, according to an embodiment of the device according to the present invention, said electrode structure comprises a cuff (e.g., out of an electrically insulating material) for enclosing said nerve to be stimulated and carrying said anodes and cathodes. Particularly said cuff extends along said axis (which may form a cylinder and/or longitudinal axis of the cuff) from a first end section of the cuff to a second end section of the cuff. Further, particularly, the cuff comprises an inside facing said nerve when the cuff encloses said nerve to be electrically stimulated.

Further, according to an embodiment of the device according to the present invention, the first anode is an annular first anode (e.g., a ring) that extends circumferentially in a peripheral direction of the cuff along said inside of the cuff on said first end section of the cuff, and wherein the second anode is an annular second anode (e.g., a ring) that extends circumferentially in said peripheral direction of the cuff along said inside of the cuff on said second end section of the cuff.

Further, according to an embodiment of the device according to the present invention, said cathodes are arranged on said inside along said peripheral direction, wherein particularly said cathodes are equidistantly spaced apart in said peripheral direction. Particularly, the cathodes may be arranged in a common plane extending perpendicular to said axis (or extending parallel to said annular anodes). Further, particularly, the anodes and cathodes are connected to the cuff such that when the cuff encloses said nerve, said cathodes and anodes contact the nerve to be stimulated.

Further, according to an embodiment of the device according to the present invention, the electrode structure comprises at least three or exactly three cathodes.

Further, according to an embodiment of the device according to the present invention, the second anode is configured to be arranged proximal to the vagus heart innervation.

Further, according to an embodiment of the device according to the present invention, the first and second anodes are asymmetrically positioned with respect to the cathodes location.

Further, according to an embodiment of the device according to the present invention, the electrode structure comprises an additional electrode located outside said cuff.

Further, according to an embodiment of the device according to the present invention, the first and the second annular electrode can also be formed out of individual segmented electrodes in a circumferential arrangement so that when they are driven in synchrony, the electrical field effectively matches that formed by a complete annular electrode.

In an alternative embodiment of the device according to the present invention, the electrode structure comprises a multi-electrode percutaneous or paddle lead (e.g., those used for SCS or PNS) with a first anode being one of the electrodes on the lead, and wherein a second anode is another electrode on the lead. The cathode is an electrode or electrodes in between the two anodes which together implement a guarded-cathode configuration for stimulation. Unlike the classical configuration, the anodes are positioned or selected to be positioned asymmetrically with respect to the cathode.

According to an embodiment of the present invention, the electrode structure comprises a percutaneous lead placed in the vicinity of the nerve. The percutaneous lead carries said at least two anodes and at least one cathode, wherein said percutaneous lead extends along an axis A.

Further, according to an embodiment of the device of the present invention, the electrode structure comprises a paddle lead carrying said at least first and second anodes and at least one cathode, wherein the paddle lead comprises an inside which faces said nerve. The at least first and second anodes and at least one cathode are located on the inside and face the nerve when the paddle lead is deployed in the patient body.

Further, according to an embodiment of the device according to the present invention, the device comprises an implantable pulse generator (IPG), the IPG comprising at least one stimulation unit or a plurality of stimulation units for generating stimulation pulses, and a control unit for controlling the at least one stimulation unit or said plurality of stimulation units, wherein the at least one stimulation unit or said plurality of stimulation units are configured to generate stimulation pulses and to deliver such stimulation pulses to at least one of: the first anode; the second anode; the respective cathode (e.g., to any of the cathodes).

Particularly, in an embodiment, the control unit may be further connected to a sub-cutaneous (sECG) sensing unit that is configured to generate a signal representing heart activity. In order to record such sECG signal, one input of this unit is preferably connected to said further electrode described above and the other input of this unit is connected to a case of the to IPG. The sECG sensing unit is configured to supply an sECG signal to the control unit. The sECG signal represents the heart activity of a patient. From this signal, inter alia a heart rate of a patient can be determined.

Further, according to an embodiment of the device according to the present invention, the implantable pulse generator (IPG) comprises a sensing front-end (e.g., comprising or formed by an amplifier) for recording evoked compound action potentials (ECAPs), wherein the first and the second anode are AC-coupled (i.e., connected via at least one capacitor) to the (e.g., inverting and non-inverting) inputs of said front-end.

Further, according to an embodiment of the device according to the present invention, for generating a desired current at one of the cathodes selected for neurostimulation, the control unit and the at least one stimulation unit or the respective stimulation unit associated to the respective (first or second) anode is configured to inject a first current as stimulation pulse through the first anode (as well as particularly a succeeding balance phase) and a simultaneous second current as stimulation pulse (as well as particularly a succeeding balance phase) through the second anode, which currents add up to said desired current that exits the selected cathode (see also below regarding suitable amounts of electrical current and particularly regarding the splitting of the current onto the two anodes).

Further, according to an embodiment of the device according to the present invention, the device (particularly control unit) is configured to adjust said currents to be injected/delivered to the respective anode, so as to adapt voltage profiles at the inputs of the front-end to one another, particularly for reducing a stimulation artifact (SA) at an output of the front-end to yield a residual SA. Particularly, due to this feature, the residual SA becomes of the same order of magnitude as the ECAP signal to be recorded, which can then be extracted from the super-imposed signal using e.g. subtraction methods or alternative processes.

Further, according to an embodiment of the device according to the present invention, for adjusting said currents, the device is configured to measure a first impedance from the first anode to a case of the implantable pulse generator (IPG), as well as a second impedance from the second anode to said case, wherein the device is configured to determine a ratio of the resistive part of the first impedance and the resistive part of the second impedance, and wherein the device (particularly control unit) is configured to adjust said currents such that a ratio of the first anode current and the second anode current corresponds to said ratio of the resistive parts of the second and the first impedance.

As mentioned before, neurons have a threshold of activation under which they cannot fire an action potential as a result of stimulation. Stimulation with amplitude below this level is referred to as sub-threshold stimulation. Above the amplitude required to activate neurons, stimulation is referred to as supra-threshold.

Further, according to an embodiment of the device according to the present invention, for extracting an evoked compound action potential (ECAP) signal, the device is configured to inject a first current in form of a sub-threshold stimulation pulse as well as a succeeding balancing phase through the first anode, and to simultaneously inject a second current in the form of a sub-threshold stimulation pulse as well as a succeeding balancing phase through the second anode, wherein said currents are adjusted such that a ratio of the first current and the second current corresponds to a ratio of the resistive part of the impedance from the second anode to a case of the implantable pulse generator (IPG) and of the resistive part of the impedance from the first anode to said case. Further, particularly, the device is configured to record the generated (sub-threshold) residual SA at the output of the front-end. Furthermore, after having injected said sub-threshold stimulation pulses, the device is configured to inject a further first current in form of a supra-threshold stimulation pulse as well as a succeeding balancing phase through the first anode, and to simultaneously inject a further second current in the form of a supra-threshold stimulation pulse as well as a succeeding balancing phase through the second anode. Also here, particularly, said further currents are adjusted such that a ratio of the further first current and the further second current corresponds to a ratio of the resistive part of the impedance from the second anode to the case of the implantable pulse generator (IPG) and of the resistive part of the impedance from the first anode to said case. Furthermore, particularly, the device is configured to record the resulting superimposed signal comprising the generated (supra-threshold) residual SA and the generated ECAP signal at the output of the sensing front-end and to subtract the (sub-threshold) SA from said super-imposed signal to obtain the desired ECAP signal. Here, the fact is used, that the sub-threshold and the supra-threshold residual SA are essentially identical.

Further, according to an alternative embodiment of the device according to the present invention, for extracting an ECAP signal, the device comprises an analog SA simulation circuit, wherein the device is configured to iteratively tune said circuit via feedback through an analog-to-digital converter (ADC) under the control of the implantable pulse generator's (IPG) control unit, wherein said tuning adjusts said circuit so that it generates waveforms which match generated sub-threshold SAs, and wherein the device is further configured to subtract an output of said circuit from an analog response signal to a supra-threshold stimulation pulse, which response signal is received by the front-end, so as to yield a resulting signal representing the desired ECAP signal.

Particularly, the final result as per the devices and methods of the present invention is a clean digital signal representing neuronal activation presence or absence which may be used for closed-loop control of the stimulation amplitude in order to optimize therapy delivery to a therapeutic window, and/or reduce side effects and unnecessary battery drain.

Particularly, the present invention provides a solution which allows acquisition of evoked neural potentials without significant distance between stimulation and recording electrodes, permitting an all-in-one nerve cuff or stimulation electrode and enabling the use of evoked compound action potentials (ECAPs) in a wide range of neurostimulation therapies where previously it was not possible. Examples include axonal stimulation targets: vagus nerve stimulation (VNS), spinal cord stimulation (SCS) using kHz stimulation, peripheral nerve stimulation (PNS), as well as somatic neuron targets: deep brain stimulation (DBS).

Particularly, the present invention will minimize the stimulation artifact (SA) as it will stop all chemical reactions that may occur during stimulation. The consumption overhead associated with information processing for the purpose of determining the adequate balancing phase shall be minimal in order not to impact the lifetime of the IPG.

Further features, aspects, objects, advantages, and possible applications of the present invention will become apparent from a study of the exemplary embodiments and examples described below, in combination with the Figures, and the appended claims.

DESCRIPTION OF THE DRAWINGS

Furthermore, detailed embodiments and features of the present invention will be described below with reference to the Figures, wherein:

FIG. 3 shows two asymmetric guarded cathode configurations according to the present invention, configuration FIG. 3A for vagus nerve stimulation (VNS) and configuration FIG. 3B for spinal cord stimulation (SCS);

DETAILED DESCRIPTION

Figure 1:
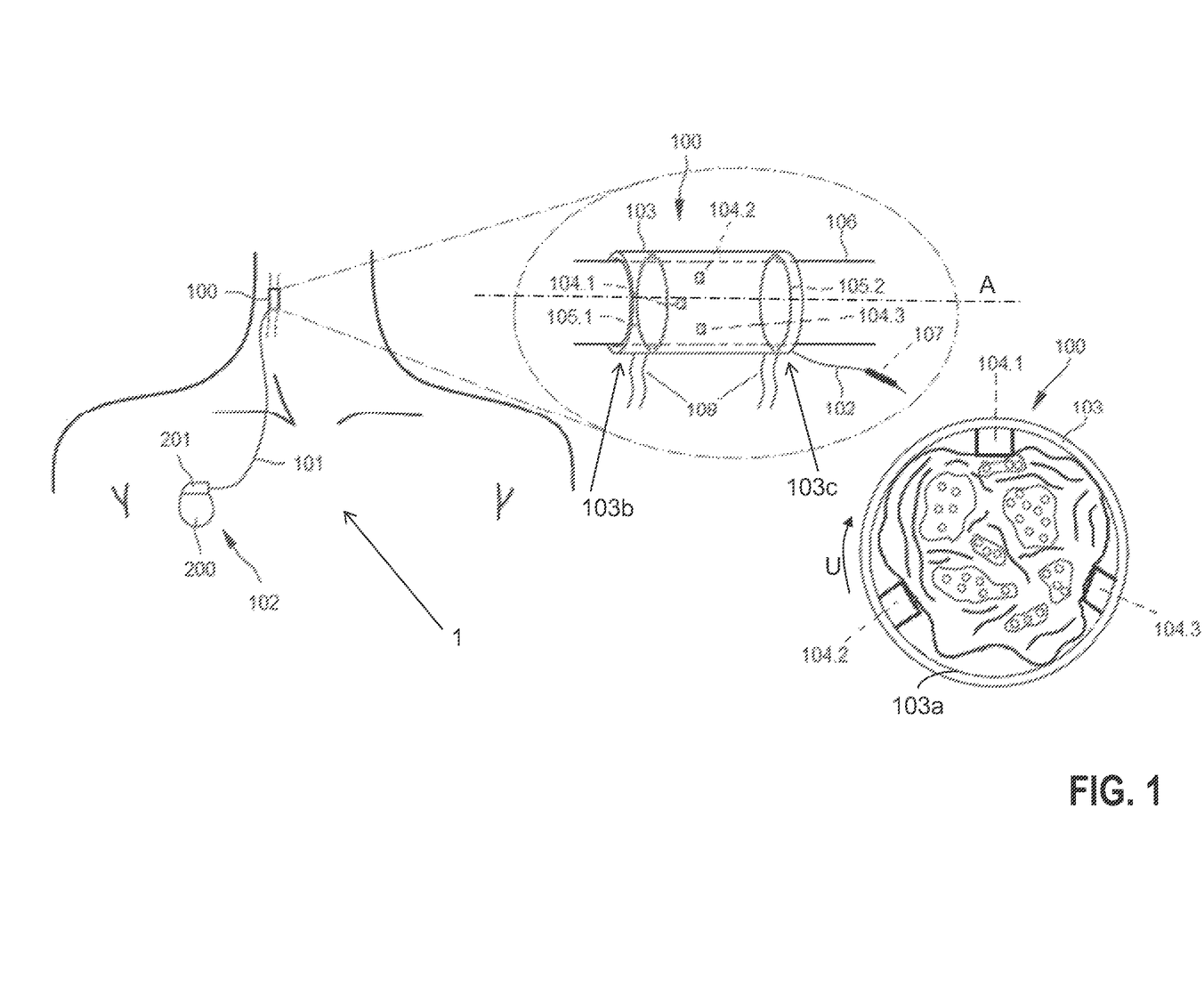
FIG. 1 shows an embodiment of a device according to the present invention.

Without losing generality, the present invention will be described using the case of vagus nerve stimulation (VNS) for congestive heart failure (CHF). VNS recently emerged as a potential progression-preventing and treatment option for CHF patients. Experimental data have demonstrated that stimulation of a vagus nerve at the cervical level is able to reverse ventricular remodeling of the failing heart. There is also evidence that increasing parasympathetic activity may stimulate the production of nitric oxide, and reduce the devastating inflammatory process involved in heart failure. Present VNS apparatuses for CHF, as 1 in FIG. 1 involve an implanted electrode structure 100, e.g., a nerve cuff electrode 100, that connects via an electrical conduit 101 (e.g., isolated wires) to an implantable pulse generator (IPG) 102 in the patient's chest as shown in FIG. 1. Particularly, the stimulation is open-loop and therapy would benefit if neural responses could be recorded utilizing the same nerve cuff electrode 100.

The same issue applies to spinal cord stimulation (SCS). Although closed-loop SCS at tonic frequencies (tens of Hz) has been proposed in prior art, neural responses can only be recorded today away from the stimulating electrodes. SCS would benefit from recording neural responses in the vicinity of the stimulating electrodes, and in particular for much higher stimulation frequencies into the kHz range.

According to a preferred embodiment of the present invention, the electrode structure 100 comprises a nerve cuff 103 that may be constructed using a silicone rubber tube 103, with e.g., centered exposed Pt/Ir, fractal Ir, or similar contacts 104 (three minimum) in its interior wall distributed circumferentially (i.e., along the peripheral direction U), and two annular rings 105.1 and 105.2 placed towards the edge (e.g., arranged on opposing end sections 103*b*, 103*c* of the cuff 103) with the latter ring 105.2 proximal to the vagus heart innervation, all in contact with the right vagus nerve 106 surface. Contacts 104.1, 104.2, 104.3 are the stimulating electrodes which are asymmetrically positioned inside the nerve cuff 103a towards the first annular anode 105.1. An additional electrode 107 is located outside the nerve cuff 103, its purpose to be described later on.

The nerve cuff 103 may be self-coiling or it may include other closing mechanisms such as a piano hinge with a nylon suture (not shown). Biocompatible strings 108 may be built on the nerve cuff 103 outer wall to open it for easy implantation around the nerve 106. In an alternative embodiment, rings 105.1, 105.2 may be formed out of individual segmented electrodes in a circumferential arrangement (i.e., along the peripheral direction U) so that when they are driven in synchrony, the electrical field effectively matches that formed by a complete ring electrode. The electrode structure 100 is connected to IPG 102, located in the patient's chest area, via a subcutaneously-implanted isolated multi-wire 101 which provides electrical connection to the contacts 104, 107 and rings 105.

Figure 2:
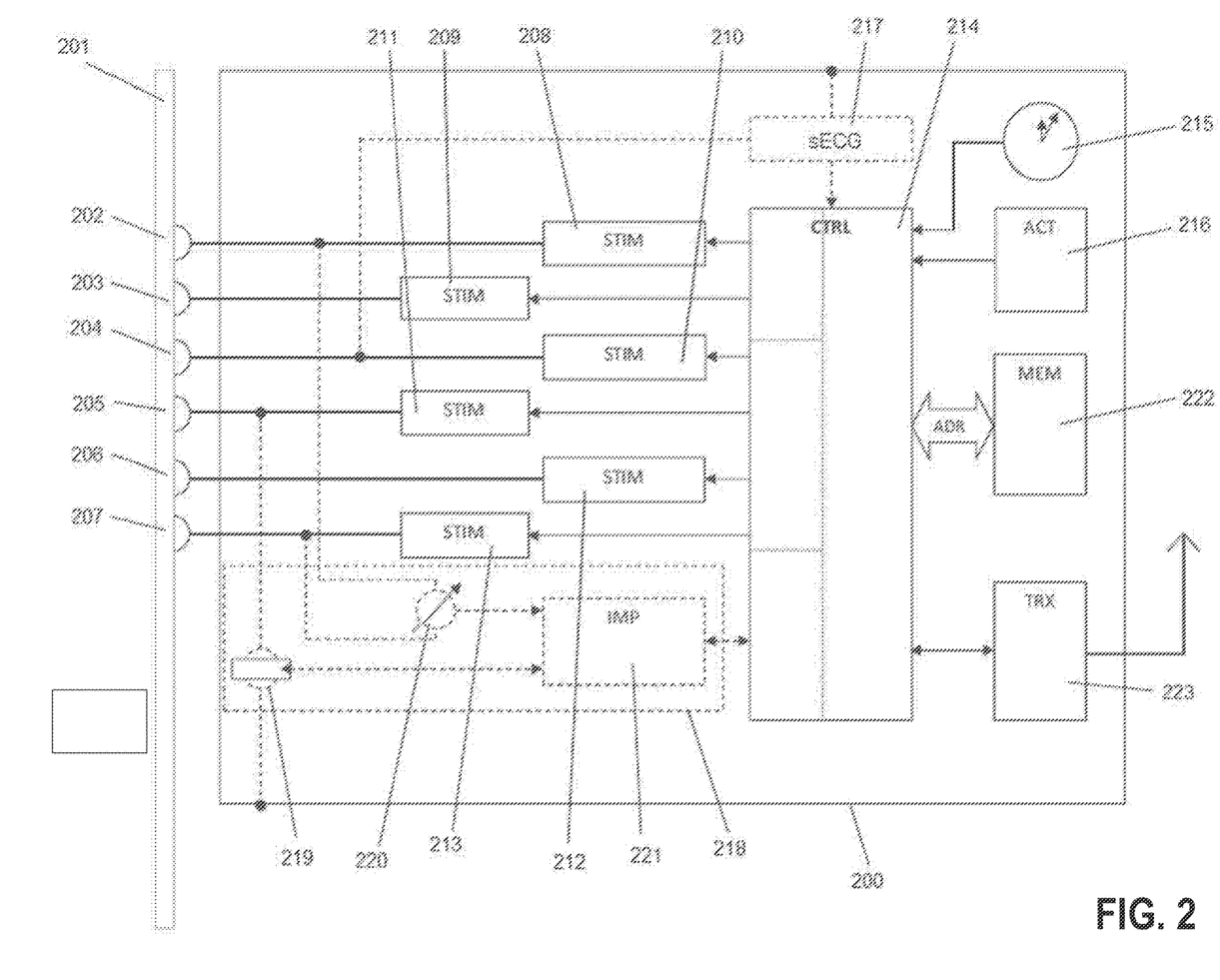
FIG. 2 shows a block diagram of an IPG that can be used with the electrode configuration according to the present invention.

As it can be taken from FIG. 2, the IPG 102 in a preferred embodiment of the present invention comprises a case (IPG case) 200 and a header 201 (see also FIG. 1) for connection of electric conduit 101. Header 201 comprises a number of connectors, in the example 202, ..., 207, that can electrically connect to connectors of the electrical conduit 101. Thus, an electric connection between connectors 202, ..., 207 and electrodes (contacts, rings, and further electrode) 104, 105, and 107 respectively, of electrode structure 100, can be made. Within the IPG case 200, one or more stimulation units 208, ..., 213 are arranged that are electrically connected to connectors 202, ..., 207 respectively, and configured to generate stimulation pulses and to deliver such stimulation pulses via a respective connector 202, ..., 207. It should be noted that instead of one stimulation unit for each connector and thus for each electrode 104, 107 and 105, a single stimulation unit and a switch matrix can be provided. In the latter embodiment, delivery of stimulation pulses via selective connectors 202, ..., 207 and thus via selected electrodes 104, 107 and 105 can be achieved by the switch matrix. In another embodiment, all contacts 104 are switched in parallel to each other and thus only one connector and one stimulation unit is needed for them. In the latter embodiment, no selection of contacts 104 for delivery of stimulation pulses is possible. Although not shown in FIG. 2, the IPG case 200 may participate in the stimulation as a return electrode.

In the embodiment of FIG. 2, each stimulation unit 208, ..., 213 is connected to and controlled by a control unit 214. Control unit 214 controls generation and triggers delivery of stimulation pulses by stimulation units 208, ..., 213. The stimulation pulses to be generated and triggered by each stimulation unit 208, ..., 213 may be tailored for vagus nerve stimulation (VNS), spinal cord stimulation (SCS), or other neurostimulation applications. Control unit 214 is further connected to a time signal generator 215 that supplies a time base to control unit 214. Further, an activity sensing unit 216 may be provided for sensing movements of the patient via movements of the IPG 102, preferably in three spatial dimensions. This activity sensor would deliver the activity signal to control unit 214.

Control unit 214 may be further connected to a subcutaneous (sECG) sensing unit 217 that is configured to generate a signal representing heart activity. In order to record such sECG signal, one input of unit 217 is preferably connected to connector 204 that connects to electrode 107 and the other input to IPG case 200. The sECG sensing unit 217 is configured to supply a sECG signal to control unit 214. The sECG signal represents the heart activity of a patient. From this signal, inter alia a heart rate of a patient can be determined.

Control unit 214 may further be connected to an impedance measuring unit 218 that comprises a constant current source 219 for generating and delivering biphasic impedance measuring pulses. Current source 219 may electrically connect to IPG case 200 and to at least one of connectors 202, ..., 207 and thus to at least one of the electrodes 104, 105 or 107 of nerve cuff electrode 100. Impedance measurement unit 218 further comprises a voltage sensing unit 220 that is configured to measure a voltage difference between at least one electrode 104, 105 or 107 of electrode structure 100 and the IPG case 200, or between at least two electrodes 104, 105 or 107, in response to delivery of current pulses by the current source 219. Current source 219 and voltage sensing unit 220 are connected to an impedance determination unit 221 of the impedance measurement unit 218. Impedance determination unit 221 is configured to generate an impedance signal depending on the voltages measured by voltage sensing unit 220 and to supply such impedance signal to control unit 214. The impedance signal generated by impedance measurement unit 218 allows assessing the status of electrodes 104, 105 and 107. Control unit 214 may be further connected to a memory unit 222 that may serve to store signals recorded by control unit 214 or programs that control the operation of control unit 214.

In order to wirelessly communicate recorded signals to an external device or to receive program instructions, at least a telemetry unit 223 is provided that is also connected to control unit 214.

Figure 3A:
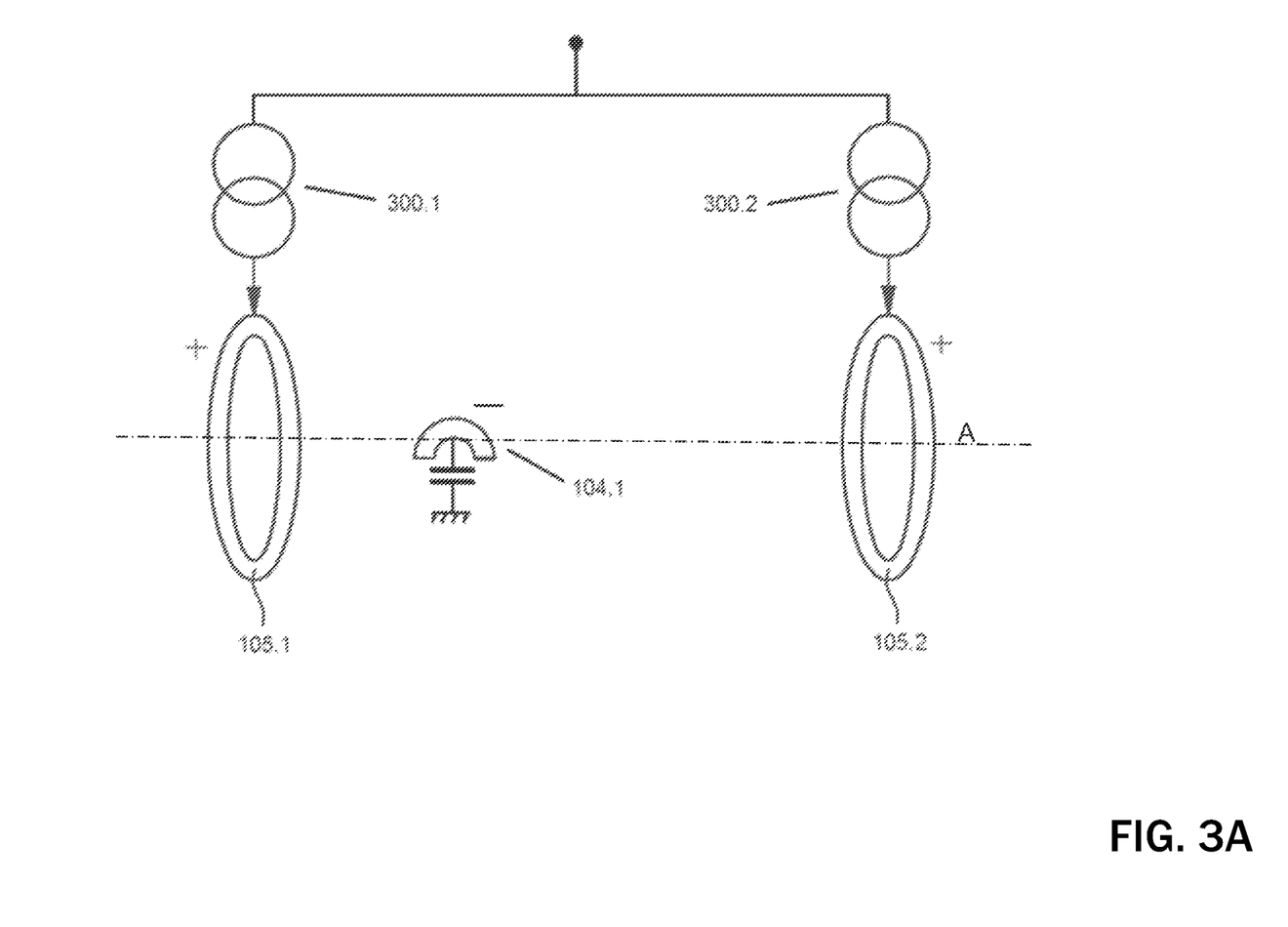
Figure 3B:
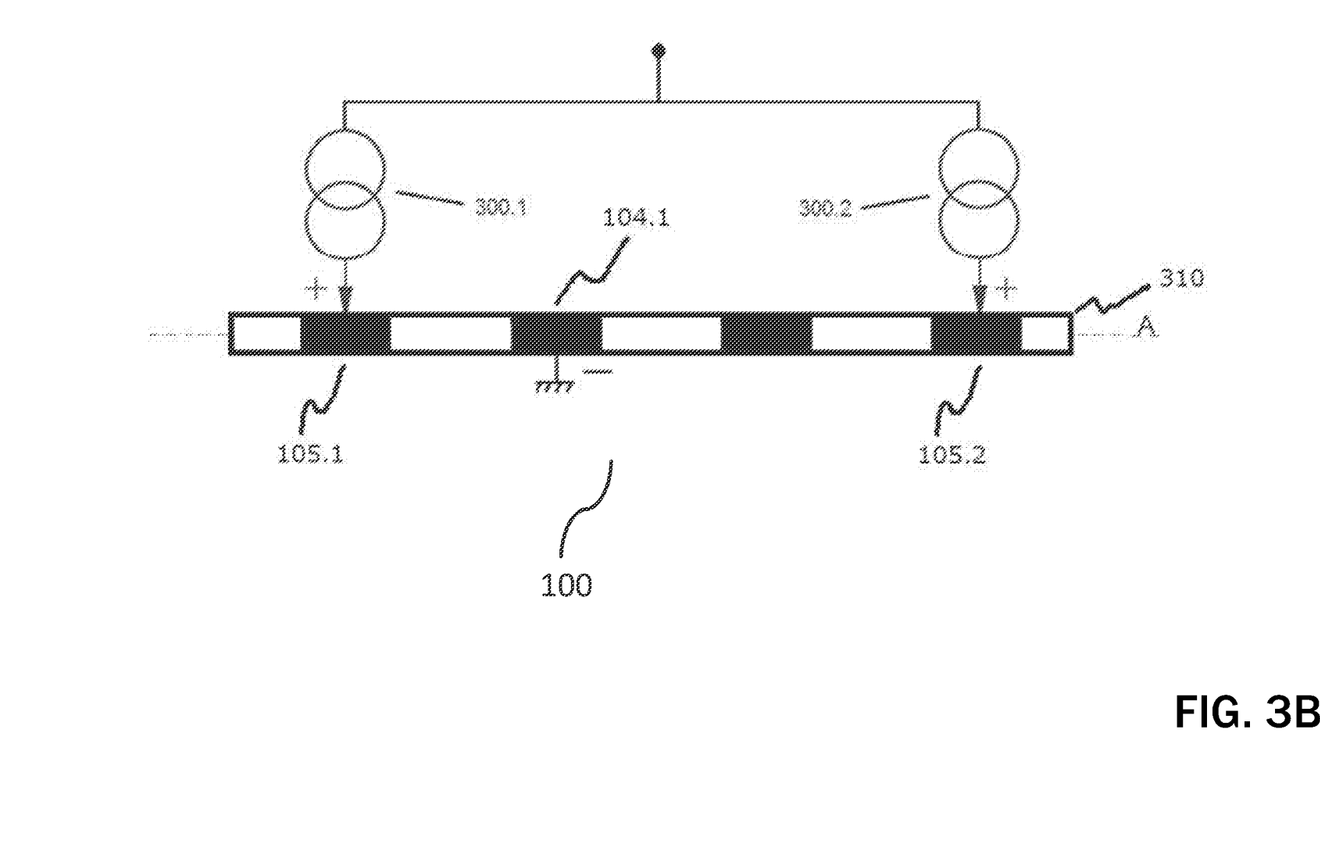

FIG. 3A shows an embodiment of a guarded-cathode configuration for delivering vagus nerve stimulation (VNS) by IPG 102, whereas FIG. 3B shows the same configuration for the case of spinal cord stimulation (SCS) via an electrode structure 100 implemented using a percutaneous lead 310. Without losing generality, let us describe the case of VNS and let us say contact 104.1 has been determined as the preferred cathode (i.e., stimulation via this electrode causes a certain reduction in heart rate with minimum stimulation side effects such as laryngeal muscle recruitment). In such case, the control unit 214 (and associated stimulation unit) splits the desired therapy current and injects electrical pulses 300.1, 300.2 (preferably current-based) via rings (i.e., annular anodes) 105. For example, if the desired therapy current is 2 mA, the control unit 214 will inject currents 300.1, 300.2 of approximately 1 mA through each ring 105.1, 105.2 so that the current exiting cathode 104.1 equals the desired 2 mA. The determination of the difference between the actual currents to flow 300.1 and 300.2 is described below.

The stimulation is preferably delivered synchronized with cardiac activity for improved therapy outcome and to minimize evoked compound action potential (ECAP) recording contamination by heart activity. ECAP recording is preferably performed during the cardiac refractory period. In the case of SCS, sECG may be recorded between the IPG case 200 and any unused electrode on the lead 310.

According to FIG. 3A, evoked compound action potentials (ECAPs) will be generated near the cathode 104.1 travelling in both directions towards rings 105.1 and 105.2. Given the maximum possible distance between cathode 104.1 and ring 105.2 (furthest apart) in a clinically-suitable electrode structure 100, the ECAP will arrive at ring 105.2 typically within 200 μs. Given stimulation pulse widths for VNS therapy are typically hundreds of μ is long, ECAP recording will overlap with the stimulation pulse itself or it associated balance phase. A similar reasoning can be applied to the configuration shown in FIG. 3B.

Given the stimulation pattern shown in FIG. 3A (the same reasoning applies to FIG. 3B), if the cathode 104.1 were centered with respect to the two rings 105.1, 105.2, and the tissue-electrode and nerve impedances were identical, the rings 105.1, 105.2 voltages would follow identical voltages during stimulation and balancing phases which could be rejected by a high common mode rejection ration (CMRR) sensing front-end. In reality, the local impedances 400.1 and 400.2 (see FIG. 4) of rings 105.1 and 105.2 and the nerve 106 respectively, will be different generating dissimilar voltages at such rings 105.1, 105.2. Further, the sensing front-end 401 is preferably AC-coupled via capacitors 402.1 and 402.2 in a preferred embodiment of the present invention to avoid direct current (DC) leakage, and although these capacitors are of the same nominal value, their actual values may be different given component tolerance. Hence, compensation is required to make the voltages at the inputs of the sensing front-end 401 follow similar voltage transitories during stimulation and balance phases so they can be rejected by the high CMRR of the sensing front-end 401.

Figure 4:
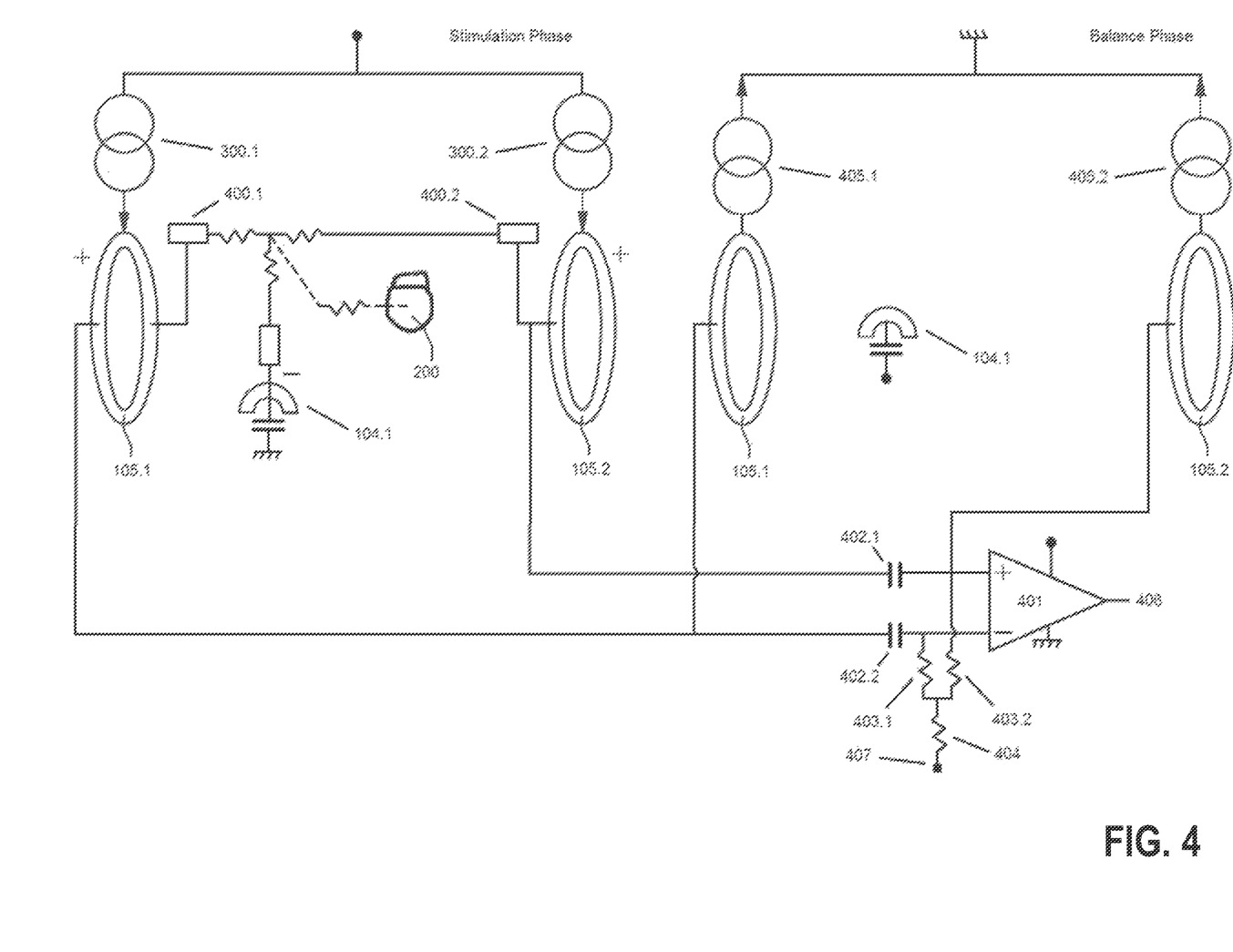
FIG. 4 shows a stimulation, balance phase, and evoked compound action potential (ECAP) sensing of a device according to the present invention.

The ECAP bandwidth of the sensing front-end 401 is typically from tens of Hz to a few kHz. Hence, capacitors 402 are in the tens of nF range whereas resistors 403.1, 403.2 (nominally equal) are in the hundred kHz range. Resistor 404 is in the tens of MΩ and permits maintaining the high CMRR of the sensing front-end 401 given tolerances in the components 402, 403. In an alternative embodiment, capacitors 402.1 and 402.2 are in the tens of pF range and resistors 403.1, 403.2 and 404 implemented via transconductors or other pseudo-resistor techniques. Amplifier 401 may utilize a chopper or similar technique for flicker noise reduction.

In another preferred embodiment of the present invention, compensation of misbalances across the components mentioned and shown in FIG. 4, to have very close voltages transitories in the inverting and non-inverting inputs of the sensing front-end 401, is performed via adjustment of currents 300.1, 300.2 for the stimulation phase (and 405.1, 405.2 for the balance phase accordingly). To calculate the required difference required between 300.1 and 300.2 (nominally split equal according to the therapy current), impedance measurements from each ring 105.1, 105.2 to the IPG case 200 are performed. Since the IPG case 200 has much larger area compared to the rings 105.1, 105.2, the impedance measurement ring 105—IPG case 200 primarily reflects the local impedance seen at each ring 105.1, 105.2. Hence, the ratio of the resistive part of these impedances is determined and currents 300.1, 300.2 are split such that their ratio corresponds to the inverse ratio of the resistive parts of said impedances and such that the total current that exits cathode 104.1 is met (depolarizing current for therapy).

For example, let's say the resistive part of the impedance from ring 105.1 and 105.2 to IPG case 200 is 1.9 kΩ and 2.0 kΩ respectively and both 300.1, 300.2 are to be programmed equal to 1 mA (i.e., 2 mA therapy current is desired). In such case, the actual current 300.1 will be programmed equal to 1,025 µA and 300.2 equal to 975 µA instead. Since the programmable currents 300.1 and 300.2 may not have the resolution necessary for compensation, auxiliary currents (not shown in FIG. 4 for simplicity) may be utilized for compensation. This compensation permits having symmetric or asymmetric balance phases (where currents 405.1 and 405.2 are adjusted accordingly). In an asymmetric balance phase the pulse width is programmed larger than the one used for stimulation resulting in lower balancing currents 405.1, 405.2. Although not shown in FIG. 4, dummy loads (resistors) may be utilized to settle the stimulation and balance currents 300 and 405 before switching them to tissue.

Figure 5:
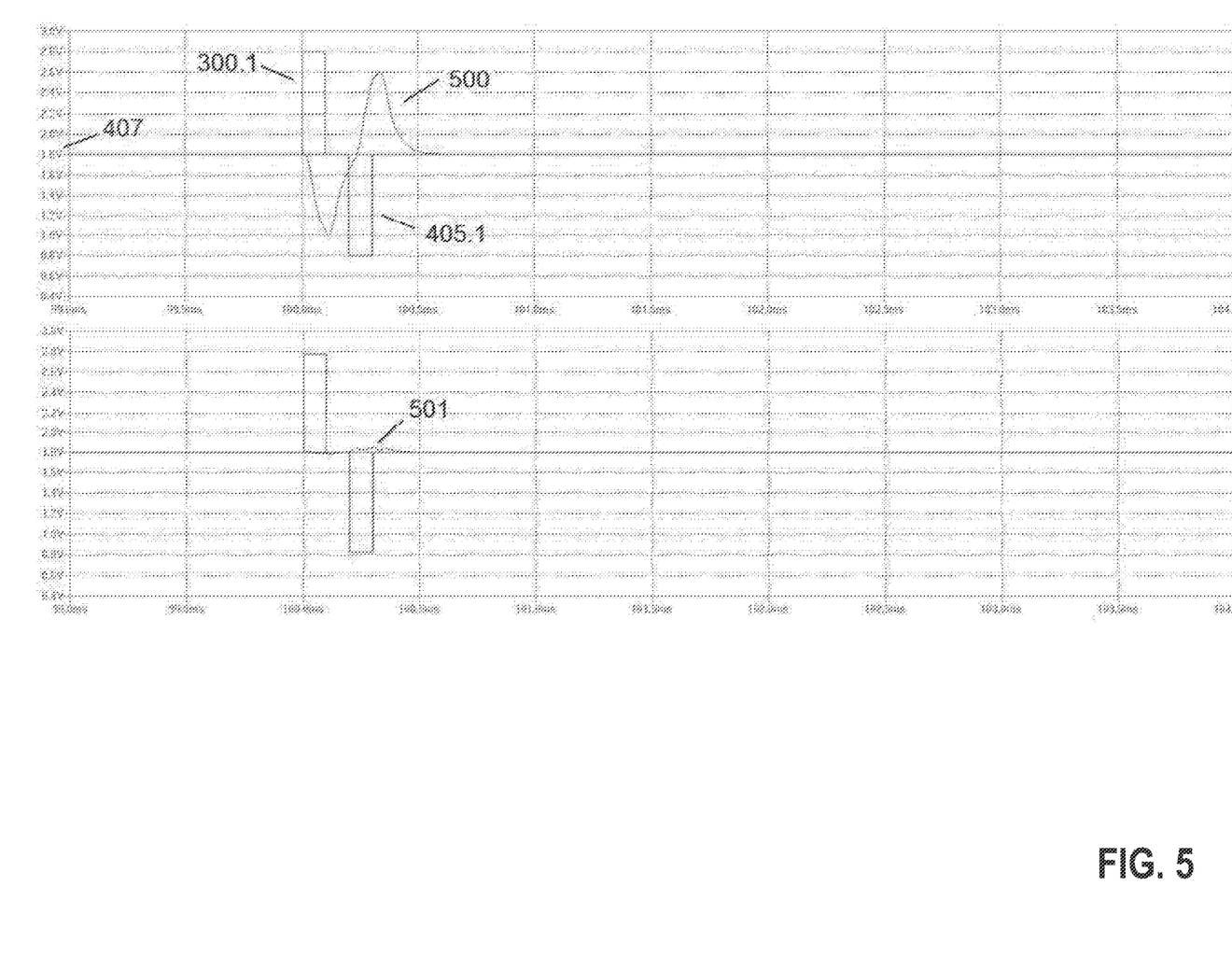
FIG. 5 shows the reduction of the stimulation artifact (SA)

FIG. 5 shows the reduction in resulting stimulation artifact (SA) at the output 406 of the sensing front-end 401 in the case, for example, of a symmetric balance phase. Note the sensing front-end 401 is neither blanked during the stimulation phase nor during the balance phase. Waveform 500 is the SA when stimulation currents 300.1 and 300.2 are both programmed with the desired nominal 1 mA whereas 501 is the SA in the case 300.1 is programmed with 975 µA and 300.2 with 1,025 µA. As it can be seen, the latter SA is significantly attenuated compared with the former staying around the reference voltage 407 in the example being described. The residual SA 501 becomes of the same order of magnitude as the evoked compound action potential (ECAP) signal to be recorded. Further methods, as described below, permit extracting a clean ECAP signal of interest.

As mentioned before, neurons have a threshold of activation under which they cannot fire an action potential as a result of stimulation. Stimulation with amplitude below this level is referred to as sub-threshold stimulation. Above the amplitude required to activate neurons, stimulation is referred to as supra-threshold.

In another preferred embodiment, the residual SA 501 as shown in FIG. 5 is first recorded and digitized (ADC) utilizing a sub-threshold stimulation pulse 300.1, 300.2 and associated balance phase 405.1, 405.2. Let's say, for example, such sub-threshold pulse is determined to be 1.5 mA through cathode 104.1. Hence, in this case, current 300.1 will be programmed as approximately 769 µA whereas current 300.2 will be programmed as 731 µA (i.e., same difference as for the 2 mA desired therapy). The sub-threshold stimulation is expected to generate a very similar SA to the supra-threshold stimulation.

Figure 6:
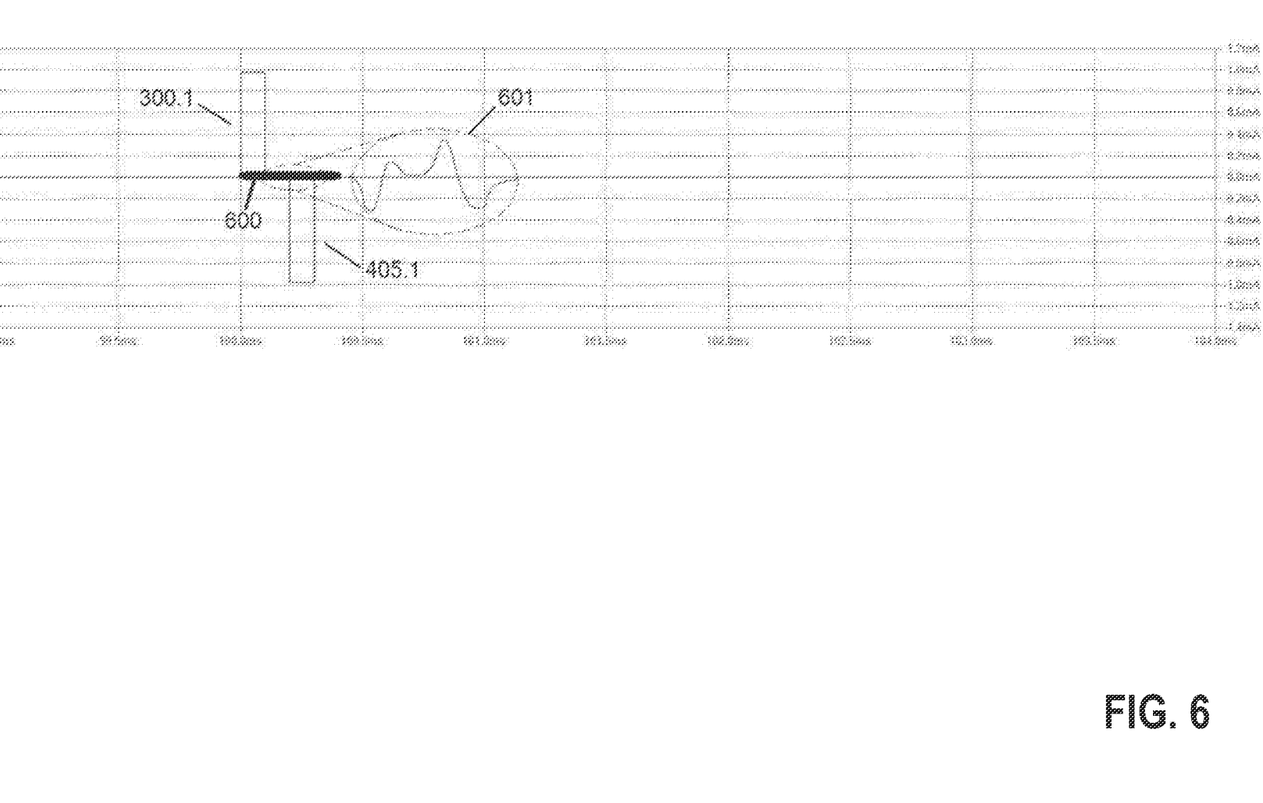
FIG. 6 shows a possible way to extract ECAPs from the residual SA.

Following this sub-threshold stimulation phase and associated balance phase, the desired supra-threshold stimulation pulse (2 mA through cathode 104.1) and balance phase are delivered, the total SA+ECAP signal (block 600, see FIG. 6) is recorded and subtracted to the sub-threshold one to obtain the desired ECAP 601. The time between the sub-threshold and supra-threshold pulses is such that the impedances can be considered invariant.

Figure 7:
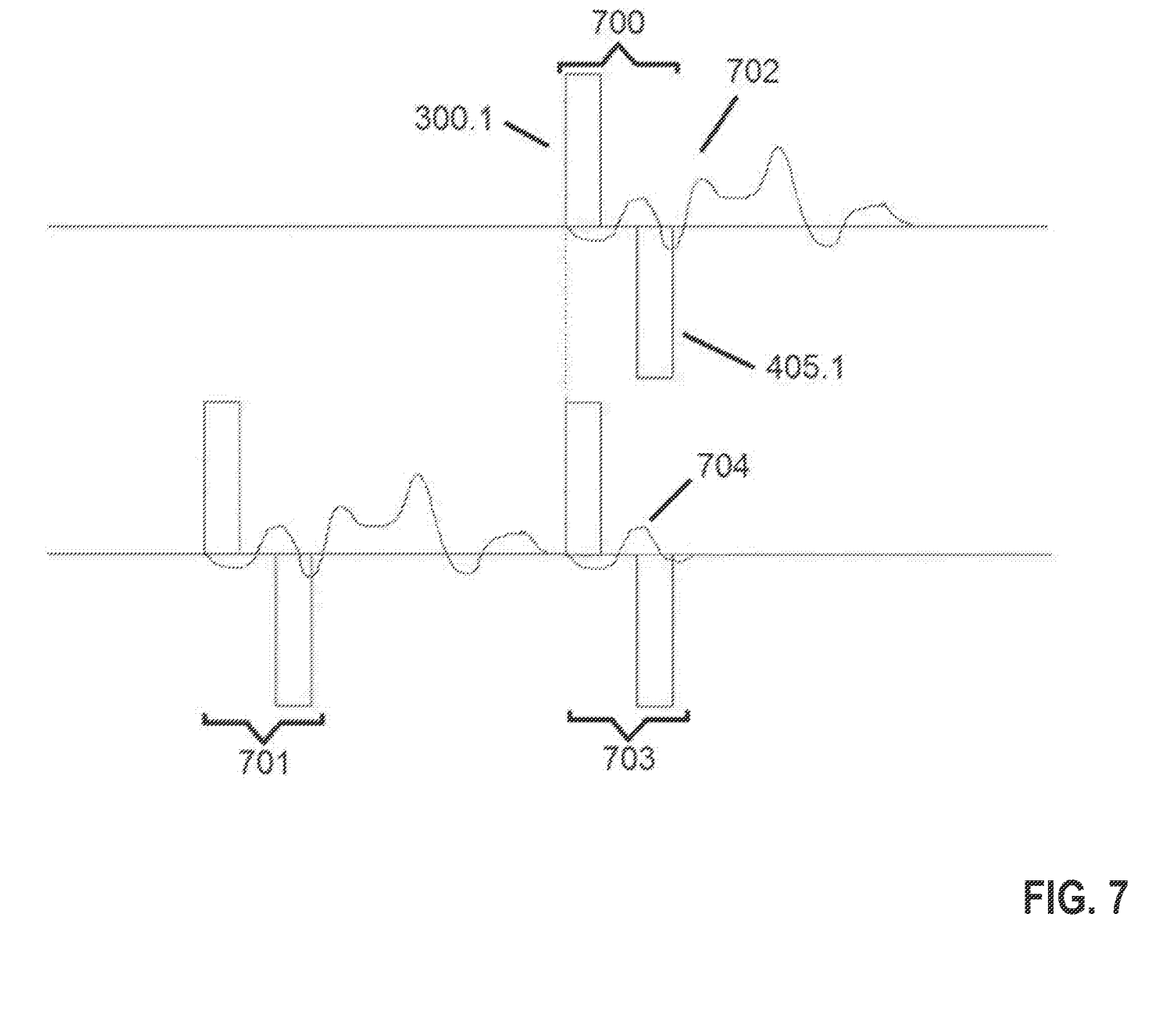
FIG. 7 shows another way of extracting ECAPs.

In an alternative embodiment, a classical forward-masking subtraction method is utilized to isolate the residual SA as shown in FIG. 7. This method utilizes two supra-threshold stimulation pulses, i.e., a probe pulse with its associated balance phase 700 and a masker pulse with its associated balance phase 701. Probe 700 is delivered first and the SA+ECAP 702 recorded and digitized. Masker 701, followed by a probe 703 (identical to probe 700) is delivered next. The time between the masker 701 and probe 703 is such that the latter is delivered during the refractory period of the fibers recruited by the former. In this way, the probe 703 only generates a residual SA 704 which is recorded and digitized. The digitized signal that contains the residual SA+ECAP 702 is then subtracted from this latter digitized signal 704 that only contains the residual SA to obtain the desired ECAP 601.

In yet an alternative embodiment, an analog SA simulation circuit is iteratively tuned via feedback through an analog-to-digital converter (ADC) under the control of the implantable pulse generator's (IPG) control unit. The tuning adjusts the analog SA simulator so that it generates waveforms which match the sub-threshold (and later, supra-threshold) SA. The output of this analog SA simulation circuit is then subtracted from the received analog signal, resulting in a signal comprised mainly of ECAPs (if stimulation is supra-threshold). This embodiment is particular useful for spinal cord stimulation (SCS) therapy delivered to the dorsal columns of the spinal cord through leads connected to an IPG as it is desirable for said IPG to determine the activation level of the dorsal columns in a dynamic way to maintain consistent stimulation. This adjustment compensates for the dynamic distance between the stimulation electrodes and the dorsal columns during normal patient activity and motion.

As mentioned before, evoked compound action potentials (ECAPs) in closed-loop SCS at tonic frequencies (tens of Hz) can only be recorded today away from the stimulating electrodes, and no prior art exists for recording ECAPs for new therapies stimulating at much higher frequencies (into the kHz range). SCS would benefit from recording neural responses in the vicinity of the stimulating electrodes for all frequencies. Any of the signal extraction methods described above, with the configuration of FIG. 3B (and associated balance phase 405.1, 405.2 not shown), can be applied to obtain ECAP signals in SCS at any frequency.

Figure 8:
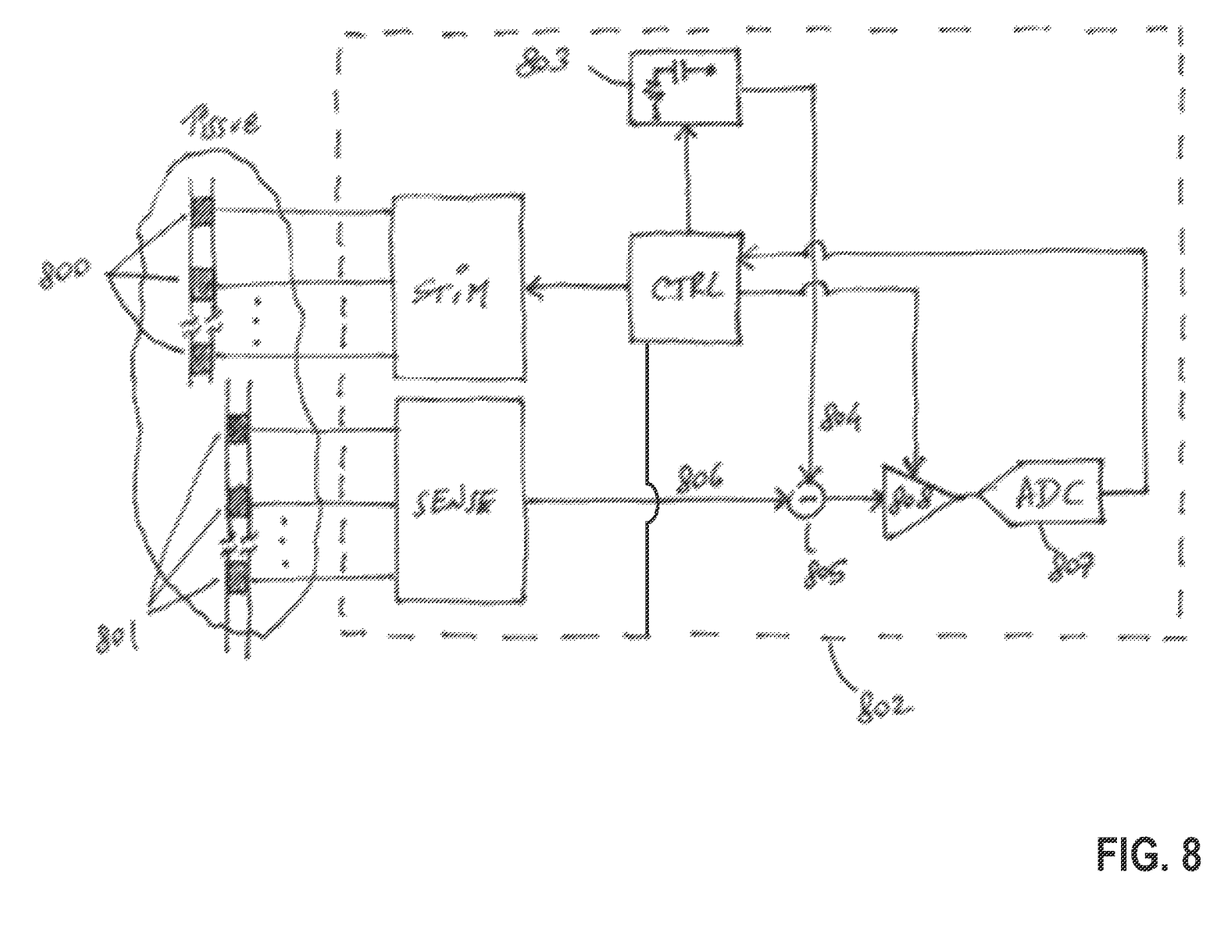
FIG. 8 shows yet another way of extracting ECAPs.

As shown in FIG. 8, this alternative embodiment stimulates (by the way of STIM block) via electrodes 800 and senses (by the way of SENSE block) on nearby electrodes 801. The IPG's 802 control unit (CTRL) tunes a SA rejection circuit by applying stimulation pulses which may be sub-threshold to the neurons of interest, building an analog cancellation parameter set which is used to control an analog SA simulation circuit 803 which generates an artificial SA matched to the recorded SA from the sensing electrodes 801. The analog SA simulation circuit 803 comprises adjustable parameters which model capacitance of electrode-tissue interfaces, tissue resistance, electrochemical reactions, and coupling components in the stimulation and recording circuitry which induce SAs via internal paths. Furthermore, the analog SA simulation circuit 803 is able to adjust its artificial SA amplitude and shape to match the amplitude of incoming SAs based on: 1) iterative model tuning and 2) programmed stimulation output amplitude. The analog SA simulation circuit 803 may be a group of switchable analog passive components, or a filtered digital-to-analog converter (DAC) which outputs a burst of samples, or a combination thereof.

This artificially produced analog SA 804 is subtracted 805 from the incoming SA signal 806 (generated by a sub-threshold pulse) such that the resulting residual SA is below the amplitude required to resolve the ECAP within the dynamic range of the ADC 807 after amplification 808.

The resulting residual, comprising remaining SA and (if stimulation is supra-threshold) ECAP, is then processed in a digital filter which subtracts remaining SA based on previous sub-threshold measurement, and compares the result with expected ECAP amplitude characteristics. Finally the decision is made whether the stimulation is supra-threshold or not, and feedback to the stimulation engine may be provided to compensate.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:
1. A device for neurostimulation comprising:
an electrode structure for delivering stimulation pulses to nerves as well as for receiving evoked compound action potentials, wherein the electrode structure comprises at least a first anode, at least a second anode opposing the at least first anode and at least one cathode arranged between said anodes, wherein said cathodes are asymmetrically arranged with respect to said first and/or second anode,
wherein the device further comprises an implantable pulse generator, the implantable pulse generator comprising at least one stimulation unit or a plurality of stimulation units for generating stimulation pulses, and a control unit for controlling the at least one stimulation unit or said plurality of stimulation units, wherein the at least one stimulation unit or said plurality of stimulation units are configured to generate stimulation pulses and to deliver such stimulation pulses to at least one of: the at least first anode; the at least second anode; the respective at least one cathode, and
wherein the implantable pulse generator comprises a sensing front-end for recording evoked compound action potentials, wherein the at least first and second anode are AC-coupled to inputs (+,−) of said sensing front-end.

2. The device according to claim 1, wherein the at least two anodes are coaxially arranged with respect to an axis, and wherein the at least one cathode is arranged spaced apart from said axis or are arranged coaxially with respect to said axis.

3. The device according to claim 2, wherein said electrode structure comprises a cuff for enclosing said nerve and carrying said at least anodes and at least one cathode, wherein said cuff extends along said axis from a first end section to a second end section of the cuff, and wherein the cuff comprises an inside facing said nerve when the cuff encloses said nerve.

4. The device according to claim 3, wherein the at least first anode is an annular first anode that extends circumferentially in a peripheral direction of the cuff along said inside on said first end section, and wherein the at least second anode is an annular second anode that extends circumferentially in said peripheral direction of the cuff along said inside on said second end section.

5. The device according to claim 4, wherein said at least one cathodes are arranged on said inside along said peripheral direction, wherein particularly said cathodes are equidistantly spaced apart in said peripheral direction.

6. The device according to claim 2, wherein said electrode structure comprises a percutaneous lead placed in the vicinity of said nerve and carrying said at least two anodes and at least one cathode, wherein said percutaneous lead extends along said axis.

7. The device according to claim 3, wherein the electrode structure comprises an additional electrode located outside said cuff.

8. The device according to claim 1, wherein said electrode structure comprises a paddle lead carrying said at least first and second anodes and at least one cathode, wherein the paddle lead comprises an inside, wherein the inside faces said nerve, where at least first and second anodes and at least one cathode are located on the inside and face the nerve when the paddle lead is deployed in the patient body.

9. The device according to claim 1, wherein the electrode structure comprises at least three or exactly three cathodes.

10. The device according to claim 1, wherein the device is configured to measure a subcutaneous electrogram between the additional electrode located outside said cuff and a case of the implantable pulse generator.

11. The device according to claim 1, wherein the evoked compound action potentials are sensed during the cardiac refractory period.

12. The device according to claim 1, wherein for generating a desired current at one of the cathodes selected for neurostimulation, the control unit and the at least one stimulation unit or the respective stimulation unit is configured to inject a first current as stimulation pulse through the at least first anode and a second current as stimulation pulse through the second anode, which currents add up to said desired current that exits the selected cathode(s).

13. The device according to claim 12, wherein for adjusting said currents, the device is configured to measure a first impedance from the at least first anode to a case of the implantable pulse generator, as well as from the at least second anode to said case, wherein the device is configured to determine a ratio of the resistive part of the first impedance and the resistive part of the second impedance, and wherein the device is configured to adjust said currents such that a ratio of the first current and the second current corresponds to said inverse ratio of the resistive parts of the first and the second impedance.

14. The device according to claim 1, wherein the device is configured to adjust said currents, so as to adapt voltage profiles at the inputs of the sensing front-end to one another, particularly for reducing a stimulation artifact at an output of the sensing front-end to yield a residual stimulation artifact.

15. A device for neurostimulation comprising:
an electrode structure for delivering stimulation pulses to nerves as well as for receiving evoked compound action potentials, wherein the electrode structure comprises at least a first anode, at least a second anode opposing the at least first anode and at least one cathode arranged between said anodes, wherein said cathodes are asymmetrically arranged with respect to said first and/or second anode,
wherein the device further comprises an implantable pulse generator, the implantable pulse generator comprising at least one stimulation unit or a plurality of stimulation units for generating stimulation pulses, and a control unit for controlling the at least one stimulation unit or said plurality of stimulation units, wherein the at least one stimulation unit or said plurality of stimulation units are configured to generate stimulation pulses and to deliver such stimulation pulses to at least one of: the at least first anode; the at least second anode; the respective at least one cathode, and
wherein for extracting an evoked compound action potential signal, the device is configured to inject a first current in form of a sub-threshold stimulation pulse as well as a succeeding balancing phase through the at least first anode, and to inject a second current in the form of a sub-threshold stimulation pulse as well as a succeeding balancing phase through the at least second anode, and wherein the device is further configured to record the generated residual stimulation artifact at the output of the sensing front-end, and wherein the device is further configured to inject a further first current in form of a supra-threshold stimulation pulse as well as a succeeding balancing phase through the at least first anode, and to inject a further second current in the form of a supra-threshold-stimulation pulse as well as a succeeding balancing phase through the at least second anode, and wherein the device is further configured to record the resulting super-imposed signal comprising the generated residual stimulation artifact and the generated evoked compound action potential signal at the output of the sensing front-end and to subtract the sub-threshold stimulation artifact associated to the sub-threshold stimulation pulses from said super-imposed signal to obtain the desired evoked compound action potential signal.

16. A device for neurostimulation comprising:
an electrode structure for delivering stimulation pulses to nerves as well as for receiving evoked compound action potentials, wherein the electrode structure comprises at least a first anode, at least a second anode opposing the at least first anode and at least one cathode arranged between said anodes, wherein said cathodes are asymmetrically arranged with respect to said first and/or second anode,
wherein the device further comprises an implantable pulse generator, the implantable pulse generator comprising at least one stimulation unit or a plurality of stimulation units for generating stimulation pulses, and a control unit for controlling the at least one stimulation unit or said plurality of stimulation units, wherein the at least one stimulation unit or said plurality of stimulation units are configured to generate stimulation pulses and to deliver such stimulation pulses to at least one of: the at least first anode; the at least second anode; the respective at least one cathode, and
wherein for extracting an evoked compound action potential signal, the device further comprises an analog stimulation artifact simulation circuit, wherein the device is configured to iteratively tune said circuit via feedback through an analog-to-digital converter under the control of the implantable pulse generator's control unit (CTRL), wherein said tuning adjusts said circuit so that it generates waveforms which match generated sub-threshold stimulation artifacts, and wherein the device is further configured to subtract an output of said circuit from an analog response signal to a supra-threshold stimulation pulse, which response signal is amplified, so as to yield a resulting signal representing the desired evoked compound action potential signal.

* * * * *